(12) United States Patent
Saito et al.

(10) Patent No.: US 9,410,908 B2
(45) Date of Patent: Aug. 9, 2016

(54) HUMIDITY MEASUREMENT DEVICE

(71) Applicant: Hitachi Automotive Systems, Ltd., Hitachinaka-shi, Ibaraki (JP)

(72) Inventors: Takayuki Saito, Hitachinaka (JP); Keiji Hanzawa, Hitachinaka (JP); Takayuki Yogo, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 228 days.

(21) Appl. No.: 14/349,602

(22) PCT Filed: Oct. 1, 2012

(86) PCT No.: PCT/JP2012/075299
§ 371 (c)(1),
(2) Date: Apr. 3, 2014

(87) PCT Pub. No.: WO2013/051488
PCT Pub. Date: Apr. 11, 2013

(65) Prior Publication Data
US 2014/0290359 A1  Oct. 2, 2014

(30) Foreign Application Priority Data

Oct. 6, 2011 (JP) .................................. 2011-221477

(51) Int. Cl.
*G01N 27/04* (2006.01)
*G01N 25/56* (2006.01)

(52) U.S. Cl.
CPC .............. *G01N 27/048* (2013.01); *G01N 25/56* (2013.01)

(58) Field of Classification Search
CPC .......... D06F 2058/2819; G01F 1/6842; G01F 1/6847; G01F 5/00; G01F 1/684; G01N 1/2247; G01N 25/56; G01N 27/048; G05D 22/02
See application file for complete search history.

(56) References Cited

U.S. PATENT DOCUMENTS

| 4,131,011 A | 12/1978 | Ling |
| 2005/0284216 A1* | 12/2005 | Tanaka ................... G01F 1/6842 73/204.26 |
| 2006/0059985 A1 | 3/2006 | Seki et al. |

(Continued)

FOREIGN PATENT DOCUMENTS

| JP | 4-77656 A | 3/1992 |
| JP | 2004-170113 A | 6/2004 |

(Continued)

OTHER PUBLICATIONS

International Search Report (PCT/ISA/210) with English translation dated Dec. 18, 2012 (Five (5) pages).

*Primary Examiner* — Daniel S Larkin
*Assistant Examiner* — Jamar Ray
(74) *Attorney, Agent, or Firm* — Crowell & Moring LLP

(57) ABSTRACT

A highly sensitive humidity measurement device is provided. The humidity measurement device has: a housing component integrally including a connector for performing input/output to/from the outside and a connector terminal component; an electronic circuit board mounted on the housing component and electrically connected to the connector terminal; and a humidity sensing element provided on the electronic circuit board. When the humidity measurement device is installed in an installation hole that is provided in a part of a main air flow passage through which suction air flows, apart of the housing component is exposed to the suction air flowing through the main air flow passage. The housing component is provided with a bypass passage to suction a part of the suction air. The bypass passage includes a bypass inlet opening that serves as a suction port of the suction air and a bypass outlet opening that discharges the suction air. The bypass outlet opening is exposed to the suction air.

12 Claims, 7 Drawing Sheets

(56) References Cited

U.S. PATENT DOCUMENTS

| | | | |
|---|---|---|---|
| 2010/0031737 A1* | 2/2010 | Saito | G01F 5/00 73/114.33 |
| 2010/0059126 A1* | 3/2010 | Diekmeyer | B60T 17/02 137/565.11 |

FOREIGN PATENT DOCUMENTS

| | | |
|---|---|---|
| JP | 2007-198893 A | 8/2007 |
| JP | 2010-151795 A | 7/2010 |
| JP | 2012-83119 A | 4/2012 |

* cited by examiner

HUMIDITY MEASUREMENT DEVICE

TECHNICAL FIELD

The present invention relates to a measurement device suitable for measuring a temperature and a humidity of suction air in an internal combustion engine.

BACKGROUND ART

As a technique to measure physical quantities of suction air for an internal combustion engine, PTL 1 describes an example of a sensor that has plural measuring functions and in which an air flow measurement device, a pressure measurement device, and a humidity measurement device are integrated.

CITATION LIST

Patent Literature

PTL 1: JP-A-2010-151795

SUMMARY OF INVENTION

Technical Problem

In general, suction air for an automobile is suctioned after floating matters in the atmosphere are removed by an air filter element that is included in an air cleaner box. Meanwhile, a filter that is fine enough to capture fine carbon and the like, for example, contained in exhaust gas is not used because large pressure loss that is caused by the air filter element and that leads to reduction in engine output and degradation of fuel consumption efficiency is not desired. Thus, the fine floating matters in the atmosphere pass through the filter and are suctioned into an engine.

In addition, engine oil that has been exposed to a high temperature and turned into steam may flow back to the air cleaner box side after the engine stop. Accordingly, it cannot be said that the air on a downstream side of the air cleaner box is necessarily clean. Furthermore, while electronic control of a diesel engine has been progressed in recent years, a fouling environment produced by the diesel engine is more severely concerned than that by a gasoline engine system.

A humidity measurement device uses a highly sensitive element to fouling; therefore, improvement in an anti-fouling property thereof is essential.

A problem of dew condensation on a humidity sensing element arises depending on a change in a humidity measuring environment. Once the dew condensation occurs on the element, a certain time is required to dry and recover the element to a normal condition, and normal measuring functions and accuracy in measurement thereof are lost during the time. In order to avoid the problem of dew condensation, it is important to ventilate the humidity sensing element and is also important for the air to constantly flow therethrough. Furthermore, the dew condensation is less likely to occur when an air flow rate is kept as high as possible. Even if the dew condensation occurs in this case, the recovery time required for the element can be reduced.

However, when the air flow rate around the humidity sensing element is increased to prevent the dew condensation, an increased amount of fouling matters floating in the air is frequently be suctioned.

In related art, as disclosed in PTL 1, a sensor element is exposed to a main air flow passage via a structure support. This configuration is characterized that, when a temperature of the suction air is abruptly changed, surface temperatures of the structure support and a sensor connected thereto are changed thereafter. Thus, if the temperature of the suction air is abruptly increased in a state that the suction air, the structure support, and the sensor element are at room temperature, for example, a temperature relationship of "the temperature of the suction air>the temperatures of the structure support and the sensor element" is established among them. The air flowing in proximity of a structure reaches a dew point due to the influence of the structure at the room temperature, and this leads a problem of the dew condensation on a surface of the structure including the sensor element. For quick recovery from the dew condensation, it is preferred to provide the sufficient air flow to the sensor element. However, because a communication hole that communicates between a measurement chamber in which the sensor is mounted and the main air flow passage is small in the structure disclosed in the related art literature, the sufficient ventilation is impossible.

In addition, the communication hole is arranged in a position at center of the main air flow passage through which the largest amount of the fouling matters pass, and a distance between the communication hole and the sensor element is short. This configuration produces many concerns in terms of practical use because the fouling matters are very likely to be adhered to the sensor element and also because the communication hole may be clogged by the fouling matters, water droplets, and the like since the communication hole is small as described above.

As described above, in order to achieve the invention, contrary properties, namely an increase in the air flow rate to prevent the dew condensation and improvement in the anti-fouling property whose importance is more emphasized with the increase in the air flow rate, need to be balanced.

The invention therefore has an object to provide a highly sensitive humidity measurement device.

Solution to Problem

In order to achieve the above object, a humidity measurement device of the invention has: a housing component integrally including a connecter for performing input/output to/from the outside and a connector terminal component; an electronic circuit board mounted on the housing component and electrically connected to the connecter terminal; and a humidity sensing element provided in the electronic circuit board. When the humidity measurement device is installed in an installation hole provided in a part of a main air flow passage through which suction air flows, a part of the housing component is exposed to the suction air flowing through the main air flow passage. The housing component is provided with a bypass passage to suction a part of the suction air, the bypass passage includes a bypass inlet opening that serves as a suction port of the suction air and a bypass outlet opening that discharges the suction air. The bypass outlet opening is exposed to the suction air.

Advantageous Effects of Invention

According to the invention, it is possible to provide a highly sensitive humidity measurement device.

DESCRIPTION OF EMBODIMENTS

Figure 1:
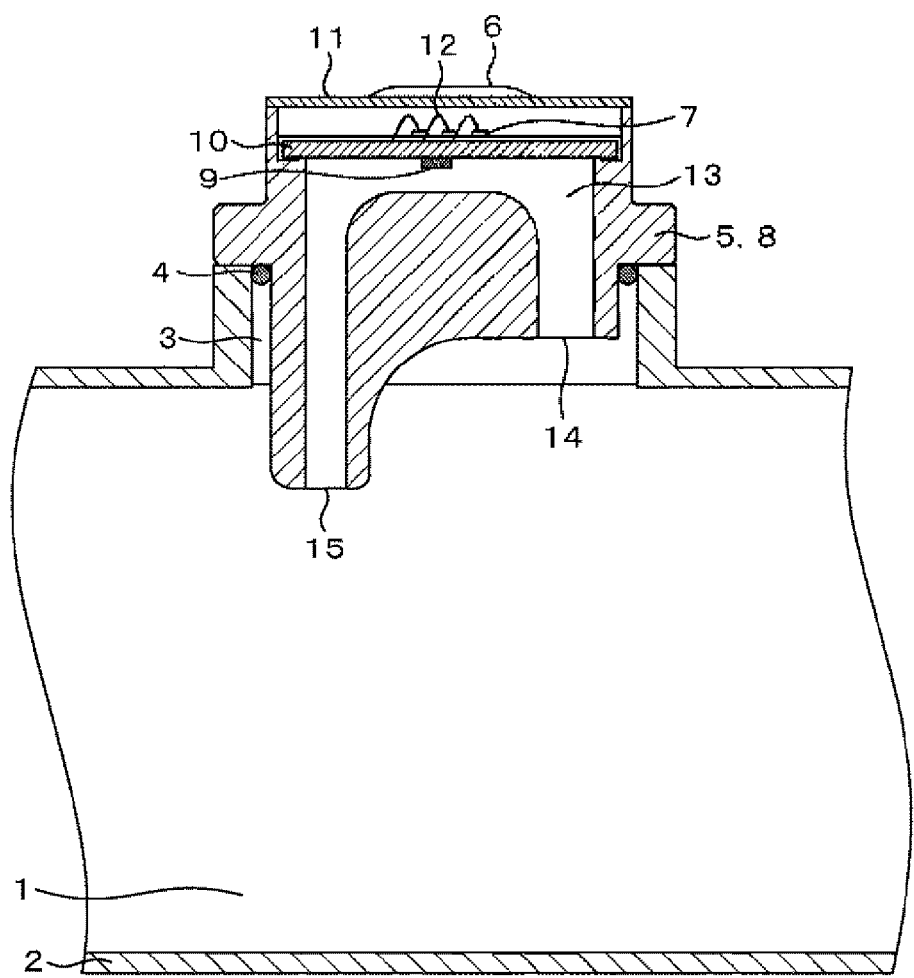
FIG. 1 is a cross-sectional view of a structure of a sensor for showing an embodiment of the invention.

A concrete example of a configuration of the invention will be described by using FIG. 1.

An air flow passage component 2 that constitutes a main air flow passage 1 is provided in a part thereof with an installation hole 3 for a sensor, and a humidity measurement device 5 is installed therein via a sealing material 4.

The humidity measurement device 5 includes: a housing component 8 as a base in which a connector 6 and a connector terminal 7 are integrally molded; and an electronic circuit board 10 on which a humidity sensing element 9 is mounted, and protects the electronic circuit board 10 such as by covering with a cover 11 and by directly casting a resin. An electrical connection between the connector terminal 7 and the electronic circuit board 10 is established by a metal bonding wire 12 to allow input/output to/from the outside via the connector 6.

The housing component 8 is provided with a bypass passage 13 to suction a part of the suction air flowing through the main air flow passage 1, and the humidity sensing element 9 is mounted to directly contact the air flowing through the bypass passage 13.

The bypass passage 13 has a bypass inlet opening 14 and a bypass outlet opening 15 that respectively serve as an air inlet and an air outlet, and only the bypass outlet opening 15 as the air outlet is inserted together with a part of the housing component 8 in the main air flow passage 1 so as to be exposed to the air flowing through the main air flow passage 1.

In this configuration, the air flow is promoted in the bypass passage 13 by using the air flow flowing along a shape of the housing component 8, which forms the bypass outlet opening 15, and by forcibly sucking out the air in the bypass passage 13 from the bypass outlet opening 15. In order to achieve a high air flow rate in the bypass passage 13, the bypass outlet opening 15 is preferably inserted in a position near the center of the main air flow passage 1 instead of a position near an inner wall surface of the air flow passage component 2 where the air flow rate is the lowest.

Most of fouling matters floating in the air have larger masses than the air, float along with a flow in the main air flow passage 1 by an inertia force, and directly pass through the installation position of the humidity measurement device 5. Particularly in this configuration, because the bypass inlet opening 14 is not arranged in the main air flow passage 1, the fouling matters are not suctioned into the bypass passage 13. Accordingly, because the improvement in the air flow rate in the bypass passage 13 and an anti-fouling property can be achieved, it is possible to provide the highly sensitive humidity measurement device.

Figure 2:
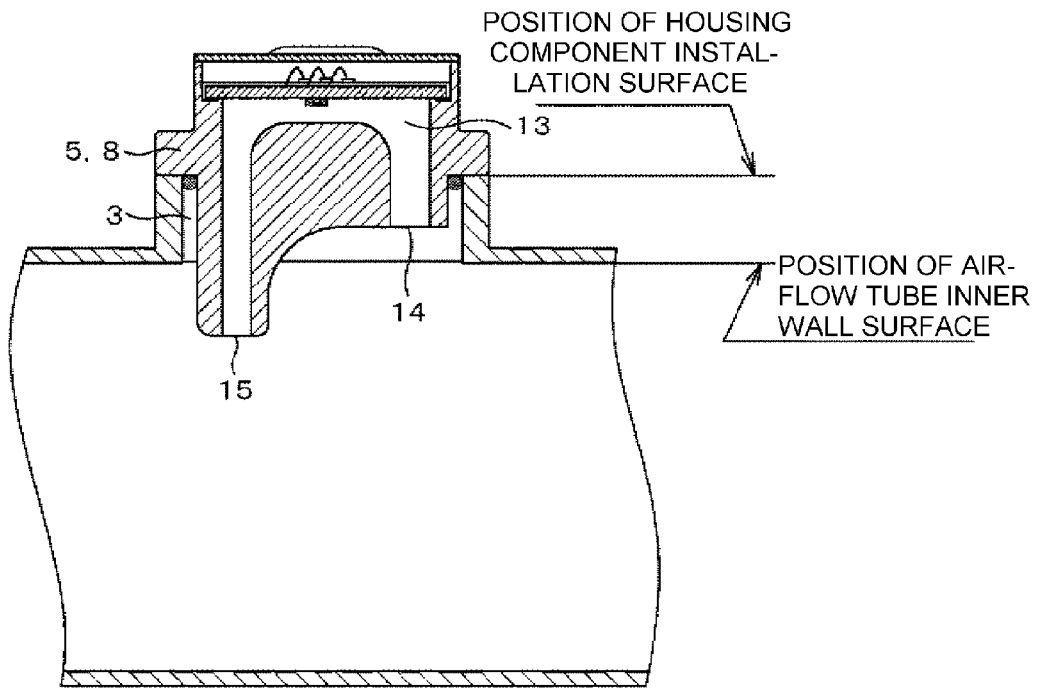
FIG. 2 is a cross-sectional view for showing another embodiment of the invention.

FIG. 2 is a cross-sectional view for showing an embodiment of the humidity measurement device 5.

The bypass inlet opening 14 of the bypass passage 13 is opened between an installation surface of the housing component 8 and a wall surface of an air flow passage component. Accordingly, the fouling matters floating in the air are not suctioned when the bypass inlet opening 14 is hidden inside, for example, the installation hole 3 to prevent direct contact with the air. In addition, the bypass inlet opening 14 is provided in a position where the air does not flow. Thus, even when an installation angle of the humidity measurement device 5 varies, such variation does not fluctuate pressure in the proximity of the bypass inlet opening 14 or the flow rate of the air flowing through the bypass passage 13.

Figure 3:
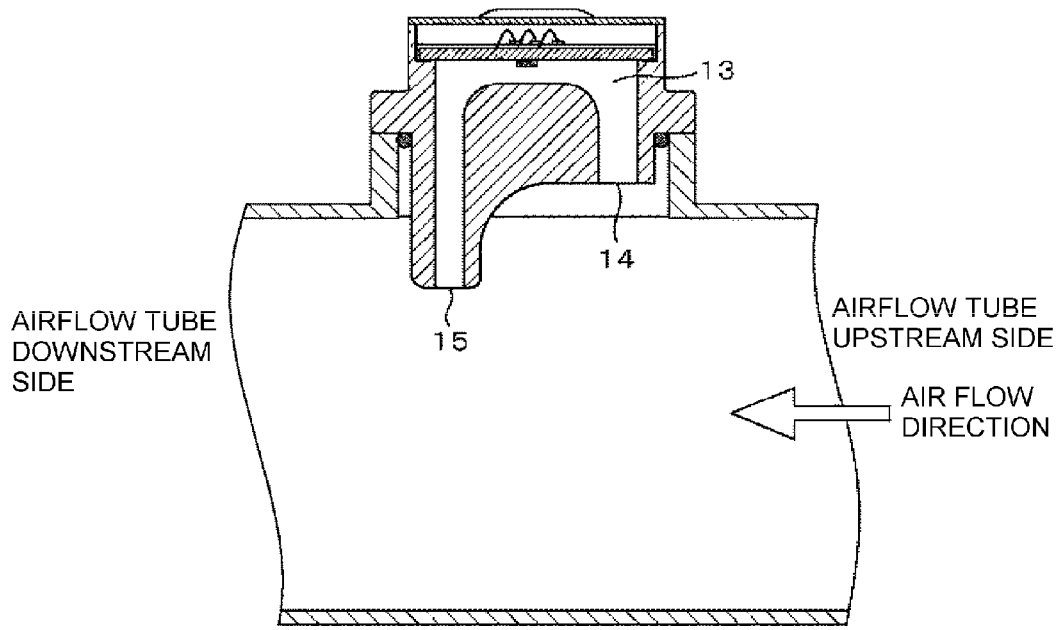
FIG. 3 is a cross-sectional view for showing another embodiment of the invention.

FIG. 3 is a cross-sectional view for showing another embodiment of the humidity measurement device 5.

The bypass inlet opening 14 of the bypass passage 13 is installed on an upstream side when seen in a flow direction of the air flowing through the main air flow passage 1 while the bypass outlet opening 15 is installed on a downstream side thereof. This configuration for installation is suitable to facilitate generation of a pressure difference that generates the air flow between the bypass inlet opening 14 and the bypass outlet opening 15, and is effective to improve the air flow rate in the bypass passage 13.

Figure 4:
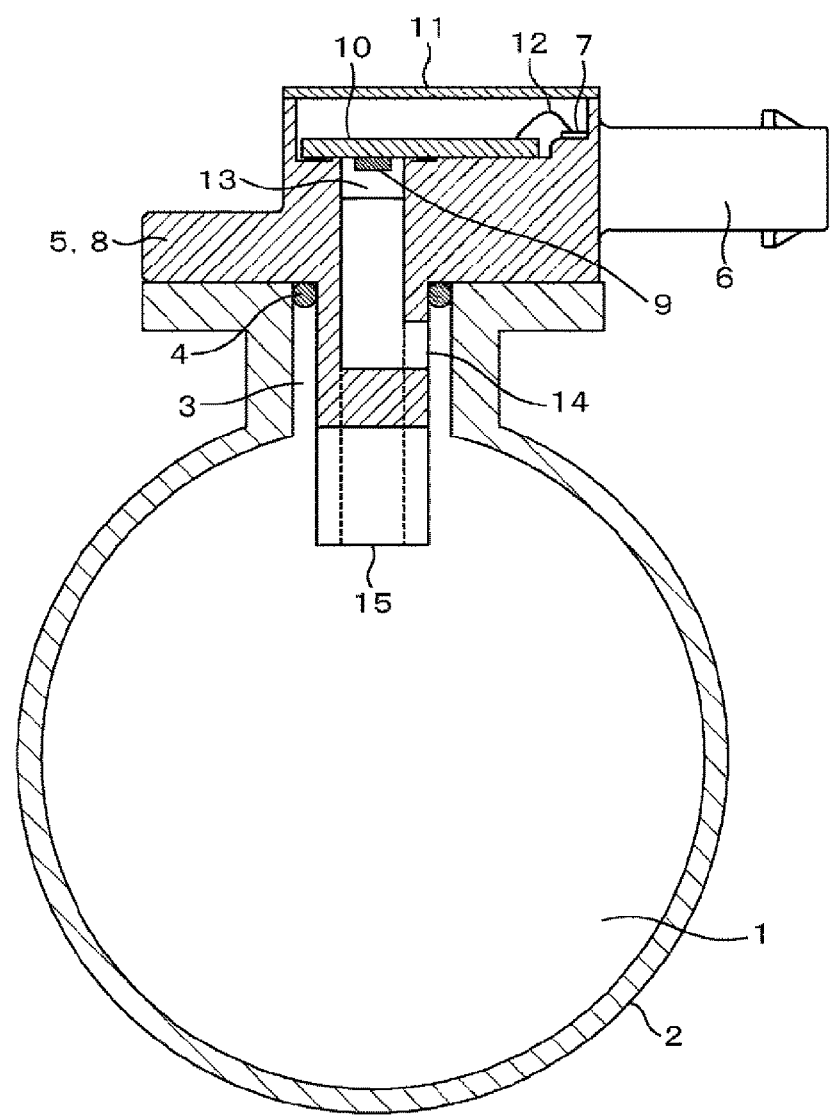
FIG. 4 is a cross-sectional view for showing another embodiment of the invention.

FIG. 4 is a cross-sectional view for showing another embodiment of the humidity measurement device 5.

A part of the air flow passage component 2 that constitutes the main air flow passage 1 is provided with the installation hole 3 to install the humidity measurement device 5 via the sealing material 4. The humidity measurement device 5 includes: the housing component 8 as the base in which the connector 6 and the connector terminal 7 are integrally molded; and the electronic circuit board 10 on which the humidity sensing element 9 is mounted, and protects the electronic circuit board 10 such as by covering with the cover 11 and by directly casting the resin. The electrical connection between the connector terminal 7 and the electronic circuit board 10 is established by the metal bonding wire 12 so as to allow the input/output to/from the outside via the connector 6.

The housing component 8 is provided with the bypass passage 13 to suction apart of the suction air flowing through the main air flow passage 1, and the humidity sensing element 9 is mounted to directly contact the air flowing through the bypass passage 13.

The bypass passage 13 has the bypass inlet opening 14 and the bypass outlet opening 15 that respectively serve as the air inlet and the air outlet, and only the bypass outlet opening 15 is inserted together with a part of the housing component 8 in the main air flow passage 1. In the installation hole 3, the bypass inlet opening 14 as the air inlet is opened in a direction orthogonal to an opening direction of the bypass outlet opening 15. In other words, it is configured that an opening surface of the bypass inlet opening 14 is positioned on a surface side that faces an inner wall of the installation hole 3.

Due to this configuration, the bypass inlet opening 14 is further less likely to suction the fouling matters floating in the air, and the anti-fouling property is thereby improved.

Next, another embodiment will be described by using FIG. 5. A description on parts of the configuration in this embodiment that are same as those in the embodiment described by using FIG. 4 will not be repeated, and only different points will be described.

Figure 5:
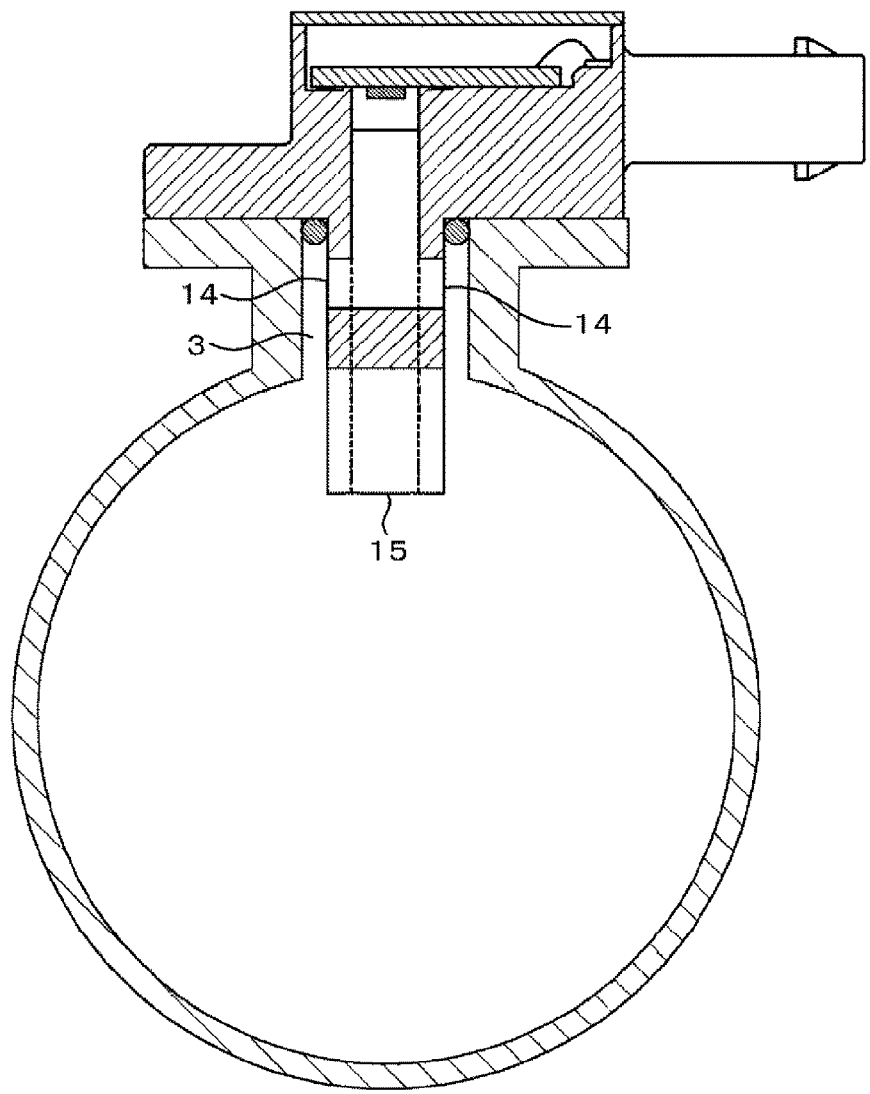
FIG. 5 is a cross-sectional view for showing another embodiment of the invention.

As shown in FIG. 5, in this embodiment, the bypass inlet opening 14 in the installation hole 3 is branched in two directions and opened in the direction orthogonal to an opening direction of the bypass outlet opening 15. In other words, it is configured that the each branched opening surface of the bypass inlet opening 14 is positioned on the surface side that faces the inner wall of the installation hole 3. Just as described, when the two inlet opening surfaces are provided, air resistance produced by the bypass inlet opening 14 can be reduced, and the air flow rate in the bypass passage 13 can thereby be improved.

Next, further another embodiment will be described by using FIG. 6. A description on parts of the configuration in this embodiment that are same as those in the embodiment described by using FIG. 5 will not be repeated, and only different points will be described.

Figure 6:
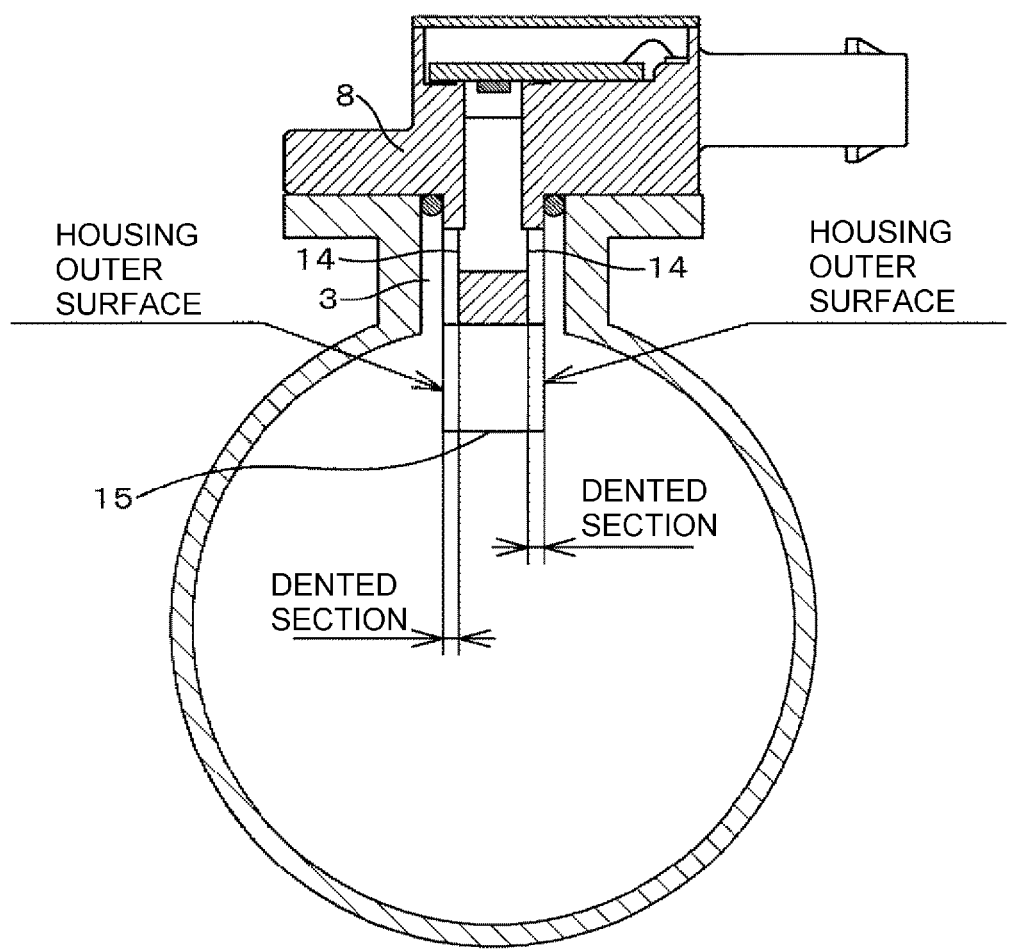
FIG. 6 is a cross-sectional view for showing another embodiment of the invention.

As shown in FIG. 6, the branched opening surface of the bypass inlet opening 14 is provided in a position that is slightly dented from an outer surface of the housing component 8. This configuration can produce an effect to relatively increase a space in the installation hole 3 between the housing component 8 and the air flow passage component 2, and this is effective in increasing the air flow rate in the bypass passage 13. In general, a relatively economical resinous material is often selected for the air flow passage component 2; however, dimensional precision of a finished product is not high. This causes variations in installation to the humidity measurement device 5, and depending on the variation, a side surface of the housing component 8, that is, the opening surface of the bypass inlet opening 14 and the lateral wall surface of the installation hole 3 may be installed in a tightly fitted manner to each other. In this case, because the bypass inlet opening 14 is sealed, the air cannot easily be suctioned, and it is thus concerned that the air flow rate in the bypass passage 13 is lowered. However, even in this case, if the opening surface of the bypass outlet opening 14 is provided in the position that is slightly dented from the outer surface of the housing component 8 as shown in FIG. 6, the air flow can surely be introduced into the bypass passage 13.

Next, yet another embodiment will be described by using FIG. 7. A description on parts of the configuration in this embodiment that are same as those in the embodiment described above will not be repeated, and only different points will be described.

Figure 7:
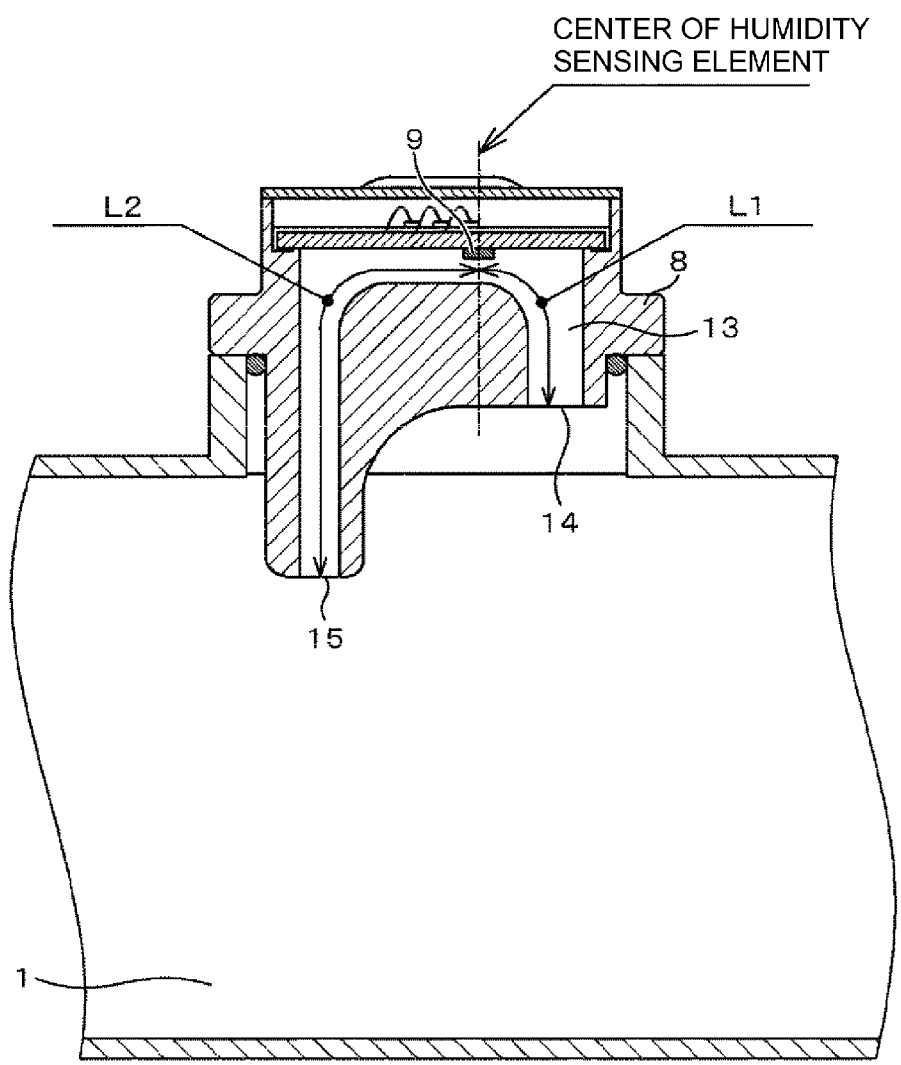
FIG. 7 is a cross-sectional view for showing another embodiment of the invention.

As shown in FIG. 7, as for a length of the bypass passage 13 provided in the housing component 8, when a distance from the humidity sensing element 9 to the opening surface of the bypass inlet opening 14 is compared to a distance from the humidity sensing element 9 to an opening surface of the bypass outlet opening 15, the distance from the humidity sensing element 9 to the opening surface of the bypass inlet opening 14 is set to be shorter than the latter. The bypass passage 13 is configured to bypass on the outside of the main air flow passage 1; therefore, when there is a large difference between a temperature of the air flowing through the main air flow passage 1 and a temperature of the outside air, the dew condensation of the air occurs in the bypass passage 13, and moisture contained in the air in the bypass passage 13 is adhered to the wall surface of the bypass passage 13. Accordingly, this causes a problem that the actual humidity of the air to be measured cannot be measured accurately. This tendency becomes particularly remarkable when the distance from the bypass inlet opening 14 to the humidity sensing element 9 is increased. On the contrary, the impact of the dew condensation is reduced as the distance from the bypass inlet opening 14 to the humidity sensing element 9 is reduced.

For use in an internal combustion engine, fouling of the humidity sensing element 9 that is caused by a reverse flow of an oil mist after the engine stop has to be considered. A degree of fouling is lowered as a distance from an inlet port of the oil mist to the humidity sensing element 9 is increased, and, because the bypass outlet opening 15 that is directly exposed to the main air flow passage 1 serves as the inlet port of the oil mist in this configuration, it is configured that the distance from the humidity sensing element 9 to the bypass outlet opening 15 is set to be long.

In order to avoid the problems of the dew condensation and the fouling, a ratio of the distance from the humidity sensing element 9 to the opening surface of the bypass inlet opening 14 to the distance from the humidity sensing element 9 to the opening surface of the bypass outlet opening 15 is preferably set to approximately 1:2.

Next, yet another embodiment will be described by using FIG. 8. A description on parts of the configuration in this embodiment that are same as those in the embodiments described so far will not be repeated, and only different points will be described.

It is desirable that the direction of the air flowing through the bypass passage 13 is parallel with the surface of the humidity sensing element 9 from the perspective of less occurrence of fouling and measurement accuracy. In this embodiment, the bypass passage 13 has two curved sections, the bypass passage 13 is configured to be straight between the two curved sections, and the humidity sensing element 9 is mounted such that it is positioned in a straight section of the bypass passage 13. In addition, due to curvature of the bypass passage 13, the air to be measured can be collected to the humidity sensing element 9 side by an effect of inertia, and this contributes to the improvement in the measurement accuracy.

Figure 8:
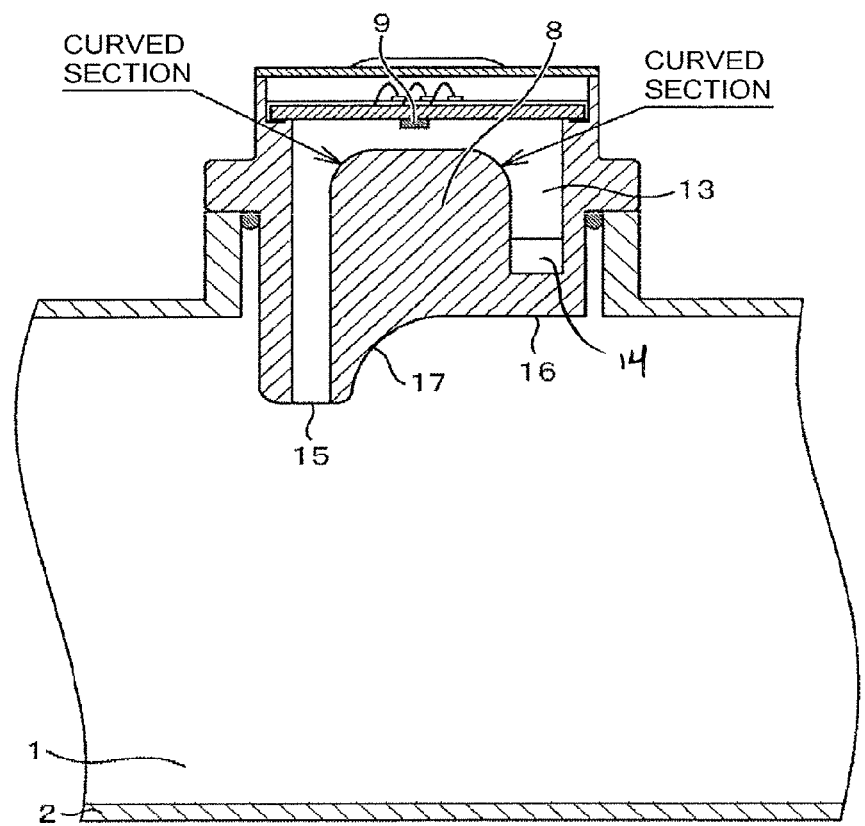
FIG. 8 is a cross-sectional view for showing another embodiment of the invention.

Furthermore, a bottom surface of the housing component 16 and the inner wall surface of the air flow passage component are substantially positioned at a same height in the configuration of FIG. 8. Moreover, when the housing component 8 is formed in a curved shape 17 from the bottom surface of the housing component 16 to the bypass outlet opening 15, a suckout effect of the air from the bypass outlet opening 15 is further increased, and the flow rate of the air flowing through the bypass passage 13 can thereby be improved. In this configuration, because the installation hole 3 is mostly filled by the structure of the housing component 8, a dead space in which excess air can stay is not formed. This further lowers a possibility of suctioning the fouling matters into the bypass passage 13.

REFERENCE SIGNS LIST

1: main air flow passage
2: air flow passage component
3: installation hole
4: sealing material
5: humidity measurement device
6: connector
7: connector terminal
8: housing component
9: humidity sensing element
10: electronic circuit board
11: cover
12: metal bonding wire
13: bypass passage
14: bypass inlet opening
15: bypass outlet opening
16: bottom surface of housing component
17: curved shape

The invention claimed is:

1. A humidity measurement device comprising: a housing component integrally including an connector for performing input from an outside of the device or output to the outside of the device and a connector terminal; an electronic circuit board mounted on the housing component and electrically connected to the connecter terminal; and a humidity sensing element provided in the electronic circuit board, in which a part of the housing component is exposed to suction air flowing through a main air flow passage when the humidity measurement device is installed in an installation hole provided in a part of the main air flow passage through which the suction air flows, wherein the housing component is provided with a bypass passage to suction a part of the suction air, the bypass passage includes a bypass inlet opening that serves as a suction port of the suction air and a bypass outlet opening that discharges the suction air, the bypass outlet opening is exposed to the suction air, and the bypass inlet opening is recessed from the main air flow passage.

2. The humidity measurement device according to claim 1, wherein an opening surface of the bypass inlet opening is provided between an inner wall surface of the main air flow passage and an installation surface of the housing component.

3. The humidity measurement device according to claim 2, wherein the bypass inlet opening is provided on an upstream side of a flow with respect to the bypass outlet opening.

4. The humidity measurement device according to claim 1, wherein an opening surface of the bypass inlet opening is provided on a surface side that faces an inner wall of the installation hole.

5. The humidity measurement device according to claim 4, wherein a second bypass inlet opening is provided on another side that faces the opening surface of the bypass inlet opening.

6. The humidity measurement device according to claim 5, wherein opening surfaces of the two bypass inlet openings are provided in positions that are dented from an outer surface of the housing.

7. The humidity measurement device according to claim 1, wherein a distance from an opening surface of the bypass inlet opening to the humidity sensing element is shorter than a distance from an opening surface of the bypass outlet opening to the humidity sensing element.

8. The humidity measurement device according to claim 7, wherein a ratio of the distance from the opening surface of the bypass inlet opening to the humidity sensing element to the distance from the opening surface of the bypass outlet opening to the humidity sensing element is 1:2.

9. The humidity measurement device according to claim 1, wherein the bypass passage has two curved sections, and the bypass passage between the two curved sections is formed to be straight, and the humidity sensing element is mounted to be positioned in a straight section of the bypass passage.

10. A humidity measurement device comprising: a housing component integrally including an connector for performing input from an outside of the device or output to the outside of the device and a connector terminal; an electronic circuit board mounted on the housing component and electrically connected to the connecter terminal; and a humidity sensing element provided in the electronic circuit board, in which a part of the housing component is exposed to suction air flowing through a main air flow passage when the humidity measurement device is installed in an installation hole provided in a part of the main air flow passage through which the suction air flows, wherein the housing component is provided with a bypass passage to suction a part of the suction air, the bypass passage includes a bypass inlet opening that serves as a suction port of the suction air and a bypass outlet opening that discharges the suction air, the bypass outlet opening is exposed to the suction air, an opening surface of the bypass inlet opening is provided on a surface side that faces an inner wall of the installation hole, and a second bypass inlet opening is provided on another side that faces the opening surface of the bypass inlet opening.

11. The humidity measurement device according to claim 10, wherein opening surfaces of the two bypass inlet openings are provided in positions that are dented from an outer surface of the housing.

12. A humidity measurement device comprising: a housing component integrally including an connector for performing input from an outside of the device or output to the outside of the device and a connector terminal; an electronic circuit board mounted on the housing component and electrically connected to the connecter terminal; and a humidity sensing element provided in the electronic circuit board, in which a part of the housing component is exposed to suction air flowing through a main air flow passage when the humidity measurement device is installed in an installation hole provided in a part of the main air flow passage through which the suction air flows, wherein the housing component is provided with a bypass passage to suction a part of the suction air, the bypass passage includes a bypass inlet opening that serves as a suction port of the suction air and a bypass outlet opening that discharges the suction air, the bypass outlet opening is exposed to the suction air, a distance from an opening surface of the bypass inlet opening to the humidity sensing element is shorter than a distance from an opening surface of the bypass outlet opening to the humidity sensing element, and a ratio of the distance from the opening surface of the bypass inlet opening to the humidity sensing element to the distance from the opening surface of the bypass outlet opening to the humidity sensing element is 1:2.

* * * * *